United States Patent [19]

Hall

[11] Patent Number: 4,774,376
[45] Date of Patent: Sep. 27, 1988

[54] PRODUCTION OF LIQUID PRODUCTS FROM ALIPHATIC HYDROCARBONS

[75] Inventor: Antony H. P. Hall, Cobham, England

[73] Assignee: The British Petroleum Company, p.l.c, London, England

[21] Appl. No.: 730,766

[22] Filed: May 3, 1985

[30] Foreign Application Priority Data

May 24, 1984 [GB] United Kingdom ................ 8413368

[51] Int. Cl.⁴ .................... C07C 15/00; C07C 2/00
[52] U.S. Cl. ................... 585/312; 585/313; 585/314; 585/315; 585/322; 585/329; 585/415
[58] Field of Search ............... 585/312, 314, 315, 322, 585/415, 310, 517, 329

[56] References Cited

U.S. PATENT DOCUMENTS

| | | | |
|---|---|---|---|
| 2,399,751 | 5/1946 | Mattox | 585/322 |
| 4,180,689 | 12/1979 | Davies | 585/415 |
| 4,304,948 | 12/1981 | Vora et al. | 585/315 |
| 4,350,835 | 9/1982 | Chester et al. | 585/415 |
| 4,367,356 | 1/1983 | Ward | 585/315 |
| 4,393,259 | 7/1983 | Ward et al. | 585/315 |
| 4,456,781 | 6/1984 | Marsh et al. | 585/533 |
| 4,487,985 | 12/1984 | Tabak | 585/533 |

FOREIGN PATENT DOCUMENTS

| | | | |
|---|---|---|---|
| 107877 | 10/1982 | European Pat. Off. | 585/415 |
| 0202000 | 11/1986 | European Pat. Off. | 585/312 |

*Primary Examiner*—Asok Pal
*Attorney, Agent, or Firm*—Brooks Haidt

[57] ABSTRACT

This invention relates to a process for producing liquid products e.g. gasoline blending components by conversion of a mixed paraffin/olefin gaseous feedstock over two types of catalysts. In a first stage, the mixed feedstock is brought into contact with a partially deactivated catalyst which converts olefins in the feed into liquid products. Gaseous products now rich in paraffins are separated and brought into contact in a second stage with another catalyst which is more active than that used in the first stage. The liquid products emerging from the second stage are thereafter separated and recovered. The catalyst is preferably a gallium oxide loaded MFI type zeolite.

15 Claims, 1 Drawing Sheet

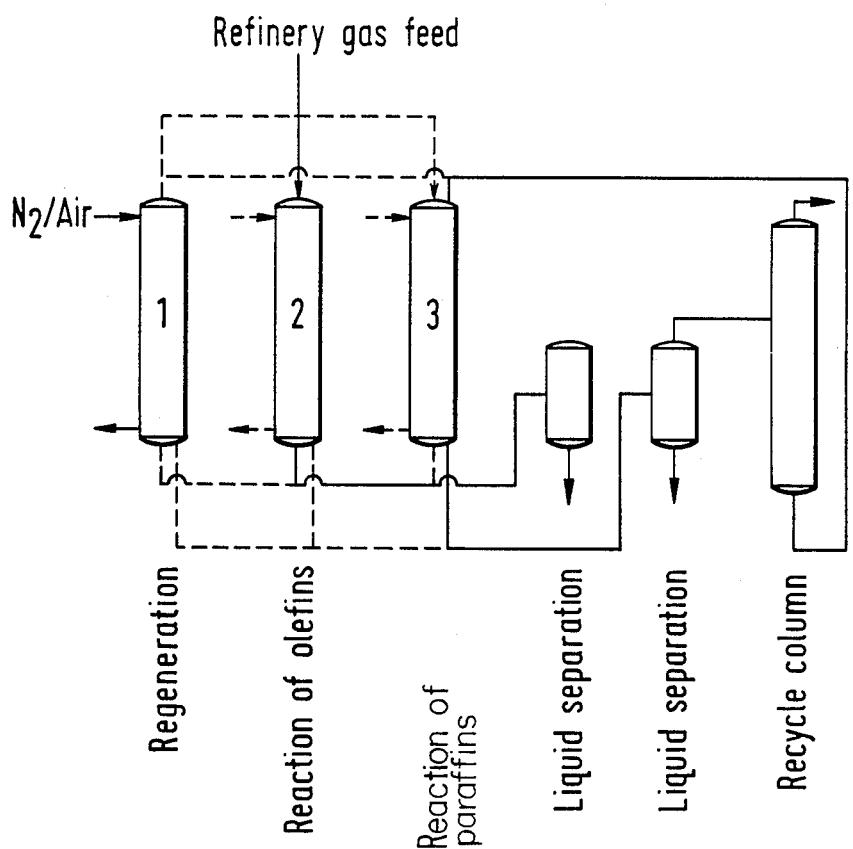
Two stage production of liquids from Refinery gas.
Reactor 1. Catalyst undergoing regeneration following for reaction of paraffins and olefins.
Reactor 2. Catalyst containing carbon after use for reactions of paraffins.
Reactor 3. Regenerated catalyst.

PRODUCTION OF LIQUID PRODUCTS FROM ALIPHATIC HYDROCARBONS

The present invention relates to a process for producing liquid products capable of being used as gasoline blending components by conversion of a gaseous feedstock comprising aliphatic hydrocarbons in the presence of a catalyst.

It is well known to convert paraffins and olefins into liquid products over a catalyst such as a gallium oxide loaded zeolite. Examples of such processes are described in our published patent specification GB No. 1561590, GB No. 2082157, EP No. 0024147, EP No. 0024930 and EP No. 0050021. However, the relative activities of the catalysts required vary with the reactant feedstock. For instance, a catalyst having a relatively higher activity is needed to convert paraffins into liquid products when compared with conversion of olefins. If the feedstock is a mixture containing significant proportions of paraffins and olefins, such as a mixture of off-gases generated by oil refineries during conventional cracking operations, it is difficult to find an optimum catalyst which will maximise the yield of liquid products from the components of such a mixture.

It is an object of the present invention to improve the processes used hitherto for conversion of a feedstock containing both paraffins and olefins into liquid products capable of being used as gasoline blending components.

Accordingly, the present invention is a process for the conversion of a mixed aliphatic hydrocarbon feedstock which is gaseous under ambient conditions into liquid products capable of being used as gasoline blending components said process comprising,
(a) passing in an olefin reaction stage the mixed feedstock over a partially deactivated catalyst,
(b) separating the reaction products from the olefin reaction stage into liquid and gaseous products,
(c) passing in a paraffin reaction stage the separated gaseous products from the olefin reaction stage over a catalyst having an activity greater than that of the catalyst in the olefin reaction stage, and
(d) separating and recovering the liquid products from the reaction products emerging from the paraffin reaction stage.

The mixed aliphatic hydrocarbon feedstock used as reactant comprises paraffins and olefins which are gaseous under ambient conditions. The mixed feedstock suitably contains at least 20%, preferably from 20-90% w/w of olefins. A typical mixed hydrocarbon feed is the $C_3$ and $C_4$ by-product stream from a fluid bed catalytic cracker which normally contains from 60-75% w/w of olefins. Such a typical feed may be mixed with a range of other refinery streams to achieve a wide variety of feed compositions.

The catalysts used for the paraffin and olefin reaction stages of the conversion reaction may be of the same or different type provided that the catalyst used in the olefin reaction stage has relatively lower activity than that used in the paraffin reaction stage. It is preferable to use the same type of catalyst and the difference in relative activities may be brought about by partial coking of the catalyst. The partial coking may, for instance, be achieved by passing an olefin or a paraffin stream over the catalyst at elevated temperature in order to deposit some carbon over the catalyst and thereby to partially deactivate the catalyst. Where coking or carbon deposition is used to partially deactivate the catalyst, the amount of carbon deposited on the catalyst is suitably from 3 to 20% w/w of the total catalyst. The deactivated catalyst so formed is then used as the olefin reaction stage catalyst and a freshly prepared or regenerated catalyst is used as the paraffin reaction stage catalyst.

In practice the mixed gas may be fed to an olefin reactor containing the partially deactivated catalyst, the paraffins in the gas acting as a heat sink to moderate the exothermic reaction of the olefins. The liquid is then separated from the product, in order to prevent degradation in the paraffin reactor, and the paraffinic gases, including some produced from the olefins in the olefin reaction stage, may then be fed to a paraffin reactor containing the newly regenerated catalyst. The liquid obtained from this paraffin reactor is separated and the mixed gas fed to a column where any residual paraffins e.g. propane and butane, are recovered for recycle. The recycle stream may return to either the paraffin reactor or to the olefin reactor, the latter being chosen if further moderation of the exothermic reaction is required. The system, with recycle to the paraffin reaction stage, is shown in simplified form in the attached diagram. In this example a swing reactor system is shown with the olefin reactor number 2 containing the partially deactivated catalyst, but the scheme is applicable to a moving bed process, in which case the mixed gas is fed to the last reactor in the train.

BRIEF DESCRIPTION OF DRAWING

In the system in the drawing, the refinery gas feed is introduced into reactor 2 containing the partially deactivated catalyst. The reaction products are then separated into liquid and gaseous products. The gaseous products from the olefin reaction stage 2 are introduced into a paraffin reaction stage reactor 3 where they are passed over a more active catalyst than the one used in the olefin reaction stage. Then, the liquid products emerging from reactor 3 are separated and recovered. The catalyst is regenerated in reactor 1 and regenerated catalyst or freshly prepared catalyst is used in reactor 3 for the paraffin reaction stage.

The reaction conditions in the two reactors may vary over a moderately wide range. Typically, in the olefin reactor, the partially deactivated catalyst suitably contains 3-20% w/w of carbon deposited thereon and the reaction is carried out at a temperature from 200°-500° C., an LHSV of 1 to 10 and a pressure of 1-20 bar absolute.

In the paraffin reactor, the catalyst is preferably a freshly produced or freshly regenerated catalyst. The reaction in this case is suitably carried out at a temperature from 400°-600° C., an LHSV of 0.5-8 and a pressure of 1-20 bar absolute.

The catalyst that may be used in the process of the present invention is preferably a gallium oxide loaded MFI-type zeolite although other catalysts known in the art as being capable of converting gaseous paraffins to liquid products may also be used.

Where a gallium loaded MFI-zeolite is used the zeolite preferably contains from 0.1 to 10% of gallium based on the total catalyst.

The gallium may be loaded onto the zeolite by well known ion-exchange or impregnation techniques. A typical example of such a process is that described in our GB No. 1561590. Instead, a gallosilicate of the type described in our EP No. 0106478 may be used as catalyst.

The typical advantages of the improved process of the present invention are that:

(a) the paraffinic components in a feed react only at temperatures above 450° C. but at these temperatures the olefinic components deposit carbon on the catalyst at a much faster rate than paraffins. Therefore the controlled two stage process diminishes problems of carbon deposition encountered by one stage processes using a single catalyst and one set of reaction conditions;

(b) the selectivity to liquid products from olefins is increased by using a lower temperature in the first stage because formation of methane and ethane is reduced; and (c) the partially deactivated catalyst for olefin conversion further reduces formation of methane and ethane. Moreover the lower overall rate of carbon deposition also reduces the frequency of catalyst regeneration and the regenerative load on the system.

The present invention is further illustrated with reference to the following Example.

EXAMPLE

A freshly regenerated galliums/zeolite catalyst was used to produce an aromatic liquid from propane at 535° C. and 6 bar absolute with a LHSV of 2. After 120 hours the conversion of propane had fallen from 65 to 55%, and the catalyst contained 4.5% weight carbon. The average conversion of propane was 60% w/w and the yield of liquid was 28.2% w/w. Butanes (1%) were also produced.

A mixture of propene (44% weight) and propane was passed over a portion of the above catalyst at 407° C./6 bar absolute with a combined LHSV of 4. The initial 98% conversion of propene fell to 90% after 75 hours on stream. The average yield of liquid over this period was 64% by weight based on the propene in the feed i.e. 28% w/w of total. The carbon deposited on the catalyst increased at a rate of 0.06 g/100 g of catalyst/hour.

In comparison, with a freshly regenerated catalyst and the same feed composition and reaction conditions, the initial 98% conversion fell to 90% over 75 hours and the liquid yield was 60% by weight. Carbon deposited on the catalyst at a rate of 0.14 g/100 g/h.

Thus the use of the catalyst already containing deposited carbon gave very similar conversions and slightly higher yields to those obtained over the freshly regenerated catalyst, and the rate of carbon deposition was less.

The residual $C_3$ and $C_4$ components accounted for 71% w/w of the total product. If these were passed to a reactor operating with the catalyst and under the conditions described above for the aromatisation of propane, then an additional quantity of liquid would be produced. This would amount to at least 28% w/w yield at 60% conversion per pass. Higher yields would be expected from the $C_4$ components because these would be expected to be more reactive. Recycle of $C_3$ and $C_4$ products would give an ultimate yield of at least 47% w/w of the residual paraffins from the olefin reactor. The total yield from the original feed would therefore be 61% w/w.

I claim:

1. A process for the conversion of a mixed aliphatic hydrocarbon feedstock which is gaseous under ambient conditions into liquid products capable of being used as gasoline blending components said process comprising, (a) passing in an olefin reaction stage the mixed feedstock over a partially deactivated catalyst, (b) separating the reaction products from the olefin reaction stage into liquid and gaseous products, (c) passing in a paraffin reaction stage the separated gaseous products from the olefin reaction stage over a catalyst having an activity greater than that of the catalyst in the olefin reaction stage, and (d) separating and recovering the liquid products from the reaction products emerging from the paraffin reaction stage.

2. A process according to claim 1 wherein the mixed feedstock comprises 20-90% w/w of olefins.

3. A process according to claim 1 or 2 wherein the mixed feedstock is the $C_3$ and $C_4$ by-product stream from a fluid bed catalytic cracking process containing 60-75% w/w of olefins.

4. A process according to claim 1 wherein the same catalyst is used in stages (a) and (c), the catalyst in stage (a) being partially deactivated by coking.

5. A process according to claim 4 wherein the partial deactivation of the catalyst in stage (a) is achieved by passing an olefin or a paraffin over the catalyst at elevated temperature in order to deposit some carbon over the catalyst.

6. A process according to claim 4 or 5 wherein the amount of carbon deposited on the catalyst of step (a) is from 3 to 20% w/w of the total catalyst.

7. A process according to claim 1 or 2 wherein the stage (a) reaction is carried out at a temperature from 200°-500° C., an LHSV of 1 to 10 and a pressure of 1-20 bar absolute.

8. A process according to claim 1 or 2 wherein the stage (c) reaction is carried out over a freshly prepared or freshly regenerated catalyst at a temperature from 400°-600° C. an LHSV of 0.5-8 and a pressure of 1-20 bar absolute.

9. A process according to claim 1 wherein the catalyst used in stages (a) and (c) is a gallium oxide loaded MFI type zeolite.

10. A process according to claim 9 wherein the catalyst contains from 0.1 to 10% of gallium based on the total catalyst.

11. A process for the conversion of a mixed aliphatic hydrocarbon feedstock which is gaseous under ambient conditions into liquid products capable of being used as gasoline blending components said process comprising, (a) passing in an olefin reaction stage the mixed feedstock over a partially deactivated catalyst, and wherein the stage (a) reaction is carried out at a temperature from 200°-407° C., an LHSV of 1 to 10 and a pressure of 1-20 bar absolute, (b) separating the reaction products from the olefin reaction stage into liquid and gaseous products, (c) passing in a paraffin reaction stage the separated gaseous products from the olefin reaction stage over a catalyst have an activity greater than that of the catalyst in the olefin reaction stage, and wherein the stage (c) reaction is carried out over a freshly prepared or freshly regenerated catalyst at a temperature above 450°-600° C., and LHSV of 0.5-8 and a pressure of 1-20 bar absolute, (d) separating and recovering the liquid products from the reaction products emerging from the paraffin reaction stage, and (e) using the same catalyst in stages (a) and (c), with the catalyst in stage (a) being partially deactivated by coking in order to deposit some carbon over the catalyst, and wherein the amount of carbon deposited on the catalyst of step (a) is from 3 to 20% w/w of the total catalyst.

12. A process according to claim 11 wherein the catalyst used in stages (a) and (c) is a gallium oxide loaded MFI type zeolite.

13. A process according to claim 12 wherein the catalyst contains from 0.1 to 10% gallium based on the total catalyst.

14. A process according to claim 1 wherein the catalyst is a gallium containing MFI-type zeolite.

15. A process according to claim 1 wherein the reaction temperature in stage (a) is from 200°–500° C.

* * * * *

UNITED STATES PATENT AND TRADEMARK OFFICE
CERTIFICATE OF CORRECTION

PATENT NO.   : 4,774,376
DATED        : September 27, 1988
INVENTOR(S)  : Anthony H. P. Hall It is certified that error appears in the above-identified patent and that said Letters Patent is hereby corrected as shown below:

Col. 3, l. 24, should read "gallium/zeolite"

Col. 6, l. 1, should read "0.1 to 10% of gallium"

Signed and Sealed this

Eighteenth Day of April, 1989

Attest:

DONALD J. QUIGG

*Attesting Officer*   *Commissioner of Patents and Trademarks*